United States Patent [19]

Oleen et al.

[11] Patent Number: 5,261,395

[45] Date of Patent: Nov. 16, 1993

[54] TOOLESS PULSE GENERATOR TO LEAD CONNECTION

[75] Inventors: Farrell G. Oleen, Princeton; John Sydorenko, St. Paul, both of Minn.

[73] Assignee: Cardiac Pacemaker, Inc., St. Paul, Minn.

[21] Appl. No.: 844,208

[22] Filed: Mar. 2, 1992

[51] Int. Cl.⁵ .................. A61N 1/00; H05G 1/00; H01R 4/50; H01R 13/58
[52] U.S. Cl. ..................... 607/15; 439/347; 439/458
[58] Field of Search ....... 128/419 P, 419 PS, 419 PG; 439/347, 458, 459, 589

[56] References Cited

U.S. PATENT DOCUMENTS

| | | |
|---|---|---|
| Re. 31,990 | 9/1985 | Sluetz et al. |
| 2,788,502 | 4/1957 | Schelke et al. ............. 439/458 |
| 3,349,364 | 10/1967 | Paullus et al. ............. 439/589 X |
| 3,683,932 | 8/1972 | Cole . |
| 3,760,332 | 9/1973 | Berkovits et al. |
| 3,871,382 | 3/1975 | Mann . |
| 3,908,668 | 9/1975 | Bolduc . |
| 3,951,154 | 4/1976 | Hartlaub . |
| 4,072,154 | 2/1978 | Anderson et al. |
| 4,105,037 | 8/1978 | Richter et al. |
| 4,112,953 | 9/1978 | Shanker et al. |
| 4,141,752 | 2/1990 | Shipko . |
| 4,142,532 | 3/1979 | Ware . |
| 4,180,078 | 12/1979 | Anderson . |
| 4,262,673 | 4/1981 | Kinney et al. |
| 4,540,236 | 9/1985 | Peers-Trevarton . |
| 4,583,543 | 4/1986 | Peers-Trevarton ............. 128/419 P |
| 4,784,141 | 11/1988 | Peers-Trevarton . |
| 4,848,346 | 7/1989 | Crawford ............. 128/419 P |
| 4,942,876 | 7/1990 | Gotthardt ............. 128/419 P |
| 4,995,389 | 2/1991 | Harris ............. 128/419 P |
| 5,000,177 | 3/1991 | Hoffmann et al. ............. 128/419 P |
| 5,086,773 | 2/1992 | Ware ............. 128/419 P |
| 5,107,856 | 4/1992 | Kristiansen et al. ......... 128/419 P X |

*Primary Examiner*—Randall L. Green
*Assistant Examiner*—Elizabeth M. Burke
*Attorney, Agent, or Firm*—Haugen and Nikolai

[57] ABSTRACT

A tooless pulse generator to lead connection for an implantable cardiac stimulator includes first and second transversely extending slots formed in the header and intersecting the lead cavities formed therein. Fitted into the rectangular slots are first and second rectangular plates, each having an elongated hole therethrough. Leaf-type springs incorporated into the rectangular slots normally urge the two plates in opposite directions causing the apertures therein to be non-aligned. By squeezing on rubber buttons affixed to the ends of the respective plates and bonded to the header, the apertures formed through the plates can be brought into alignment, allowing the lead body and the proximal pin to be easily inserted through the aligned openings and into the connector block. When the squeezing force is released, the springs again urge the apertures in the plates out of alignment and, in doing so, they deform the plastic sheath of the lead body and tightly grip same to prevent the leads from being pulled free of the lead cavities formed in the header even when a tension force of about three lbs. is applied to the leads.

5 Claims, 3 Drawing Sheets

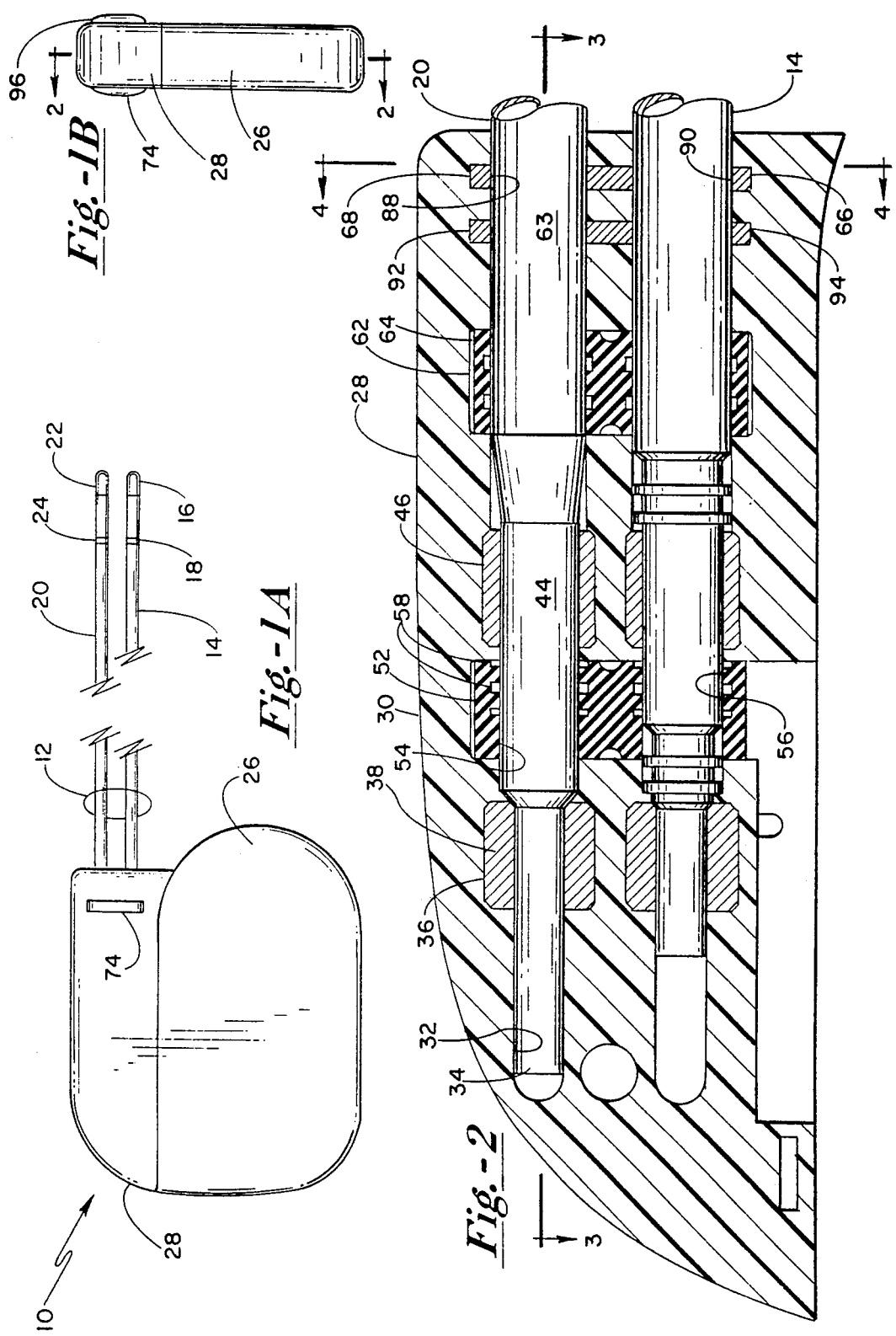

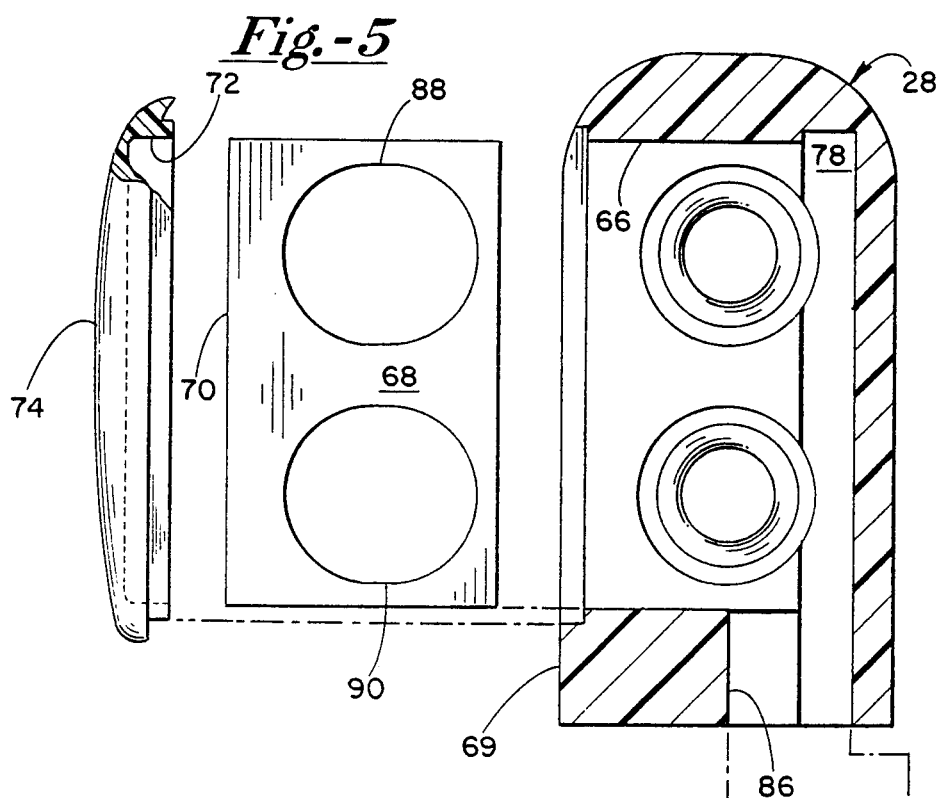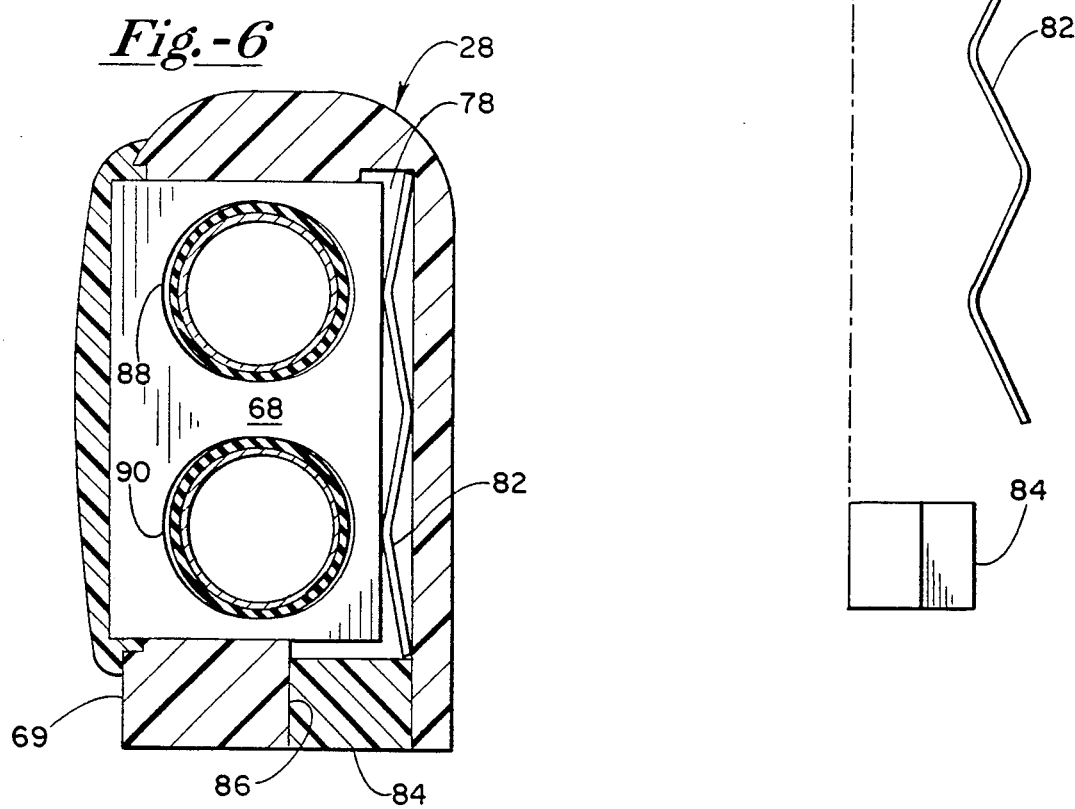

TOOLESS PULSE GENERATOR TO LEAD CONNECTION

BACKGROUND OF THE INVENTION

I. Field of the Invention

This invention relates generally to implantable tissue stimulating apparatus, such as cardiac pacemakers, cardiac defibrillators and related devices, and more particularly to an improved method of securing the proximal terminal pin and ring of the stimulating lead in the female jacks of the electrical stimulating pulse generator.

II. Discussion of the Prior Art

Implantable stimulating devices, such as cardiac pacemakers, automatic implantable cardiac defibrillators, and myostimulators generally comprise electronic sensing and pulse generating circuitry and associated power sources housed within a body member formed from a suitable metal and commonly referred to as the "can". Passing through the can's top surface in a hermetically sealed manner are electrical feed throughs, which are arranged to conduct electrical signals into and out from the circuitry sealed within the metal can. Affixed to the top surface of the can and surrounding the feed throughs is a molded plastic body having one or more longitudinal bores formed therein for receiving the proximal end male connector of the implanted flexible leads used to convey electrical stimulating pulses from the implanted pulse generator to the tissue to be stimulated and for conveying physiologic signals or myopotentials picked up by the lead's distal electrodes and carried back to the pulse generator electronic circuit. The bores in the body member communicate with electrical contacts that mate with pin and ring-type connector terminals on the proximal end of the leads. Typically, setscrews or other threaded fasteners pass through threaded bores oriented transverse to the lead receiving bores in the body member and in the connector block to maintain the lead's proximal terminal pin and ring in fixed or locked relation relative to the connector blocks coupled to the feed throughs in the body member of the pulse generator.

A typical example of the prior art lead connection heretofore used in the cardiac stimulating field is shown in the Ware U.S. Pat. No. 4,142,532 which, in FIG. 2 thereof, shows a can 13 with feed throughs 19 embedded in a molded plastic header 25, the feed through being electrically coupled to a terminal block 40 having longitudinal bores 41 and 45 formed therein for receiving electrical leads having pin and ring-type male terminals 21 surrounded by an insulating sheath 22 preferably formed from silicon rubber or other suitable medical grade plastic. A setscrew 47 threaded into the terminal block 40 is designed to engage the terminal pin 21 to firmly lodge it in place. Plugs 48 then fit into the screw axis holes 53 to preclude the influx of body fluids and/or body tissue.

Other examples of the prior art similar to the disclosure of the Ware U.S. Pat. No. 4,142,532 described above are the Kinney et al. U.S. Pat. No. 4,262,673 and the Anderson et al. U.S. Pat. No. 4,072,154.

While the prior art techniques for securing stimulating leads to implantable pulse generators have proved reliable, they suffer from the defect that they require the attending physician to handle small parts, such as the setscrews and the seal plugs and also require the use of a screw driver or an allen wrench to install and tighten down the setscrews onto the lead's terminal pins. Thus, a need exists for a method of coupling the proximal terminals of cardiac stimulating leads to an implantable pulse generator which does not require the handling of small parts or the use of special tools to perfect the connection. The Peers-Trevarton U.S. Pat. Nos. 4,540,236 and 4,784,141 each describe quick-lock-/quick-release connectors for implantable cardiac stimulators, but in each instance, a special, non-standard lead is involved. For example, in the '236 patent, the lead incorporates a plunger body 34 on the proximal end of its terminal pin and the plunger fits into a socket having a plurality of spring fingers for effectively gripping the plunger body. The device can be released by pressing on an elastomeric diaphragm 40 which serves to move the plunger and spread the spring fingers so that they no longer lock relative to the terminal pin. The mechanism described in the Peers-Trevarton patents are unduly complex and, hence, may prove unreliable with time.

It can be seen, then, that a need still exists for a way of rapidly and reliably coupling standard implantable stimulating leads to its associated pulse generator in a way that will reduce the surgeon's time and undue complications for making this connection while eliminating the setscrews, seal plugs and a special setscrew wrench. Moreover, the approach used must preclude an electrical leakage path occasioned by body fluid seepage into the lead to feed through coupling zone.

OBJECTS

It is accordingly a principal object of the present invention to provide an improved tooless pulse generator to lead connection for implantable tissue stimulators, such as cardiac pacemakers and automatic implantable cardiac defibrillators which have the above-listed desirable properties.

Another object of the invention is to provide an implantable tissue stimulating device having means for receiving the proximal end portion of the implantable leads used to deliver the stimulation current and to sense cardiac physiological activities, which requires no tools to establish a reliable coupling between the lead and pulse generator terminals whereby the lead is retained in place in a reliable manner.

SUMMARY OF THE INVENTION

In accordance with the present invention, the tooless connector includes a connector header which is preferably premolded and which incorporates one or more lead cavities therein, each of the lead cavities containing a pin connector block and a ring connector block to electrically unite the male lead's connector pin and ring connector, respectively, to the connector blocks contained within the lead cavities.

Formed adjacent the entry to the lead cavities and opposite each other are two rectangular grooves which extend perpendicular to and intersect the lead cavities in the connector body. Inserted into each of the rectangular cavities is a rectangular plate that contains a slot therethrough, the slot having generally semicircular ends of a diameter only slightly larger than the diameter of the lead body. Also fitted into the rectangular cavities along with the rectangular plates are leaf springs which normally urge the two plates outward in opposite directions. Affixed to the outer ends of the rectangular plates and fitted into the entry slots formed in the header are deformable rubber buttons. By compressing the two rubber buttons on opposite side surfaces of the connector body, the slots in the two plates become longitudinally aligned which allows the lead connectors to be inserted into the lead cavity. When the finger pressure on the rubber buttons is relieved, the leaf springs move the rectangular plates so that the circular slots therein are no longer aligned and the edges defining the slots press into the deformable plastic material comprising the lead body to tightly grip the lead body and hold it in locked relationship relative to the electrical terminals contained in the connector body. Should it be desired that the leads be removed from the implanted pacer, it is only necessary to again squeeze the two rubber buttons to align the slots therein with one another and now the lead can readily be pulled free from the cavity in which it had earlier been inserted.

As will be explained in greater detail below, the lead grip mechanism incorporated into the pulse generator's header is simple in its operation and requires no tools for insertion, removal and retention of the lead within the pulse generator's connector body. The counterbalancing compressive forces of the spring biased plates maintain the lead axis aligned with the lead cavity axis, thus satisfying the requirements of certain international standards which had been developed and which apply to implantable cardiac pacemakers and defibrillators.

DESCRIPTION OF THE DRAWINGS

The foregoing features, objects and advantages of the invention will become apparent to those skilled in the art from the following detailed description of a preferred embodiment, especially when considered in conjunction with accompanying drawings in which like numerals in the several views refer to corresponding parts.

FIG. 1a is a side elevation of an implantable cardiac rhythm management device in accordance with the present invention;

FIG. 1b is a left end view of the device of FIG. 1a;

FIG. 2 is a greatly enlarged longitudinal sectional view of the header which incorporates the present invention taken along the line 2—2 in FIG. 1;

FIG. 5 is an exploded view of the parts illustrated in the sectional view of FIG. 4; and FIG. 6 is a further sectional view taken along the line 4—4 in FIG. 2 when the plates therein are squeezed to cause the elongated apertures in the two plates to become aligned.

DESCRIPTION OF THE PREFERRED EMBODIMENT

Figure 3:
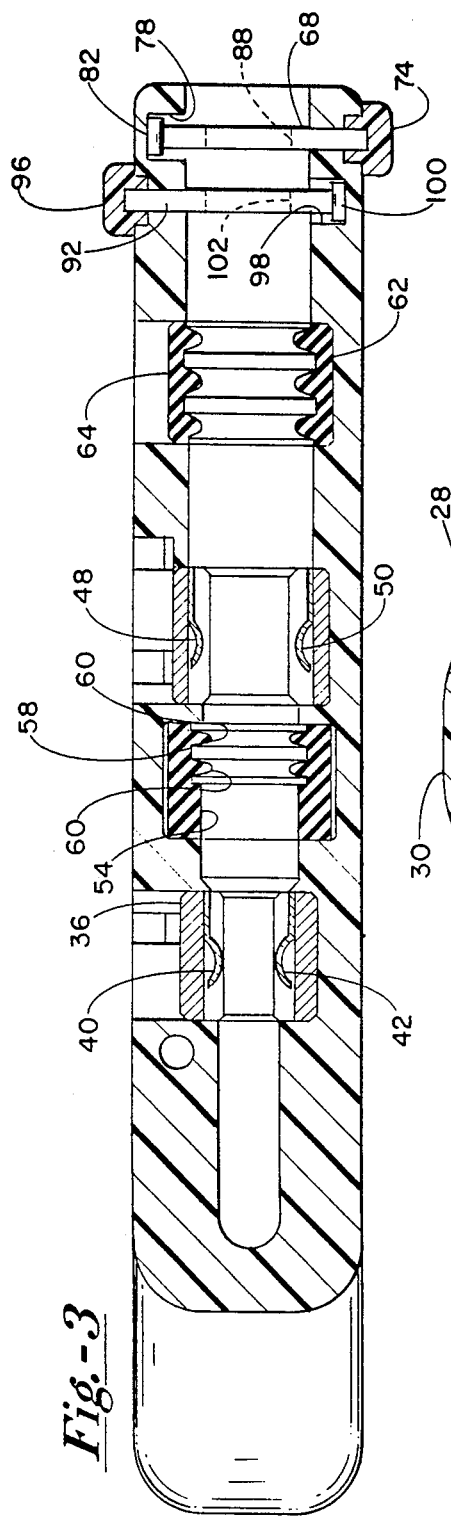
FIG. 3 is a cross-sectional view taken along the line 3—3 in FIG. 2 but with no leads present in the header.

Referring to FIG. 1, there is indicated generally by numeral 10 an implantable electrical stimulator, such as a cardiac pacemaker. The device of FIG. 1 will typically be implanted in a surgically created pocket beneath the skin in the chest area of the patient and one or more leads 12 are routed through the vascular system until the electrodes on the distal end thereof are appropriately placed relative to the cardiac tissue to be stimulated. The device of FIG. 1 is illustrated as being a dual chamber pacemaker, meaning that stimulating and sensing electrodes are placed in both the right atrium and right ventricle of the heart. The atrial lead is identified by numeral 20 and it includes a stimulating tip electrode 22 and a ring-type surface electrode 24 for sensing cardiac depolarization signals in the atrium. Likewise, the ventricular lead 14 is routed through the vascular system until its distal tip electrode 16 is located at the apex of the right ventricle with the ring-type surface electrode 18 located proximally thereof, but still within the right ventricular chamber.

The electronics (not shown) comprising the pacemaker sensing, pacing and control circuitry along with a battery power source is contained within a sealed metal housing referred to as the can and identified by numeral 26. Affixed to the top surface of the can 26 is a header 28, the details of which will be described in considerably greater detail hereinbelow, in that the tooless connector of the present invention resides within the header 28.

Referring now to FIG. 2, a vertical cross-section through the header 28 is shown. It comprises a molded plastic body 30, preferably formed from a medical grade plastic, such as polyurethane, polycarbonate or epoxy, and which includes a plurality of lead receiving cavities, each with internally formed recesses for receiving the connector blocks and seals for electrically joining the electrodes 16, 18, 22 and 24 on the distal end of the lead body to the circuitry within the pacer can 26 and for maintaining a fluid-tight seal to prevent ingress of body fluids which might compromise that electrical connection. The lead cavity for lead 20 includes a first cylindrical portion 32 for receiving a male terminal pin 34 on the proximal end of the lead 20. An enlargement of cylindrical cavity 32 identified by numeral 36 has a metal connector block 38 resident therein, the connector block 38 having first and second spoon-shaped spring contacts 40 and 42 (FIG. 3) internal thereto for engaging the metal surface of the male connector pin 34.

With reference again to FIG. 2, the lead 20 further includes a coaxially disposed metal ring 44 which surrounds but is insulated from the pin 34. The ring 44 is electrically connected by an elongated, flexible conductor (not shown) which passes through the length of the lead body to the ring electrode 24 near the distal end of the lead 20. Cooperating with the metal ring 44 is a further connector block 46 formed from an appropriate metal and having spoon-shaped spring contacts 48 and 50 (FIG. 3) which engage its metal surface to provide the internal connection between the lead terminal and a feed through pin (not shown) with which the connector block 46 is associated. This feed through pin passes through an appropriate hermetic seal in the can to mate with the internal electronic circuitry in a known fashion.

There is still a further cavity formed in the connector body 28 for receiving an elastomeric seal member 52 therein. The inner seal member 52 is preferably formed from medical-grade elastomer and includes a pair of apertures 54 and 56 extending through the thickness dimension thereof. The apertures have a series of longitudinally spaced grooves as at 58 formed inwardly to define intermediate protruding segments as at 60 in FIG. 3. When a lead is inserted through its cavity so that the pin 34 is fully inserted, the annular ridges 60 wipe against the lead's contact surface 44 creating a lip seal to effectively block fluid flow therebeyond that might otherwise contaminate the integrity of the electrical contact between the spring fingers 40 and 42 of the connector block 38 and the metallic terminal 34 and cause an electrical current leakage between connector blocks 38 and 46.

In much the same fashion, the lead cavities in the header 28 include a further recess 62 into which is fitted a further elastomeric seal member 64 configured much like the seal member 52, except that it cooperates with a portion of the lead 20 identified by numeral 63 that is covered with an outer layer of a low durometer deformable plastic, such as silicon rubber. The seal member 64 also has a plurality of grooves and flutes like the seal member 52. These are more visible in the view of FIG. 3. The outer seal 64 cooperating with the insulating surface of the lead 20 inhibits or prevents the ingress of body fluids beyond the seal to prevent corrosion of the metallic contacts established between the spoon-shaped connector elements 40–42 and 48–50 with the mating metallic surfaces of the lead terminals and maximize the electrical resistance between the electrical contacts and the body tissue.

Rather than utilizing setscrews or the like to lock the leads 14 and 20 within their respective lead receiving bores or cavities, in accordance with the present invention, a self-contained, tooless locking mechanism is used.

Figure 4:
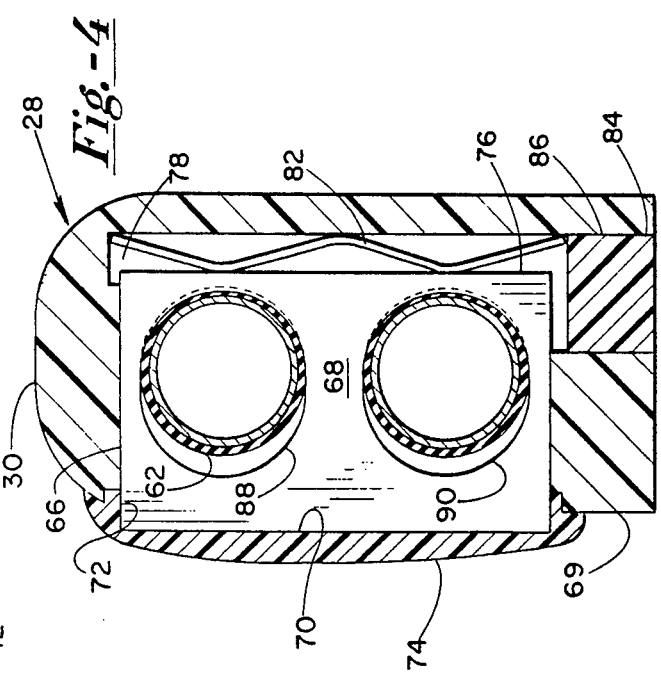
FIG. 4 is a cross-sectional view taken along the line 4—4 in FIG. 2.

Referring to FIG. 4 which shows a cross-section of the header 28 taken along the lines 4—4 in FIG. 2, a generally rectangular slot 66 is formed inward from a side surface 69 of the molded plastic member 30 for receiving a rigid polymer or metal rectangular plate 68 therein. The plate 68 has a first edge 70 which extends laterally outward beyond the edge 69 of the header and it fits into a slot 72 formed in an elastomeric button-like cover 74 that is adhesively bonded into an opening formed in the side edge 69 of the header.

The edge 76 of the plate 68 opposite to edge 70 projects into an enlarged cavity 78 formed in the header and abuts a leaf spring member 82. With reference to FIG. 5, the spring member 82 may be inserted into the cavity 78 from the bottom before the plug member 84 is inserted into an opening 86 in the header 28 and adhesively bonded in place.

The plate 68 is seen to include a pair of elongated circular apertures or slots 88 and 90 formed by two eccentrically displaced semicircles which are only slightly larger in diameter than the outside diameter of the segment 63 of the lead 20 and the corresponding segment of the lead 14. In FIG. 4, the leaf spring 82 biases or urges the plate 68 to be left so that the edges of the slots 88 and 90 press against and slightly into the soft plastic of the lead bodies on their right-hand side when viewed as in FIG. 4.

Referring again to FIGS. 2 and 3, it can also be seen that a similar spring biased plate 92 fits into a rectangular slot 94 formed into the molded plastic header 28 from its right-hand side and has that edge covered by an elongated rubber button 96. Slot 94 is parallel to and spaced from slot 66. The edge of the plate 92 opposite the rubber button 96 fits into a recess or cavity 98 containing a leaf spring 100 which normally presses against the edge of plate 92 to urge that plate to the right when viewed as in FIG. 3. The plate 92 like its corresponding plate 68 includes an elongated generally circular opening 102 formed therein of a size permitting the lead segment 63 with its insulation covering to pass through that aperture. However, when the force of the spring 100 is acting on the plate 92, the edge of the aperture on the left presses against and slightly into the deformable plastic insulation coating when the lead properly inserted into its lead cavity.

When inserting a lead into its lead cavity, the implanting surgeon need only squeeze the rubber buttons 74 and 96 between his thumb and forefinger to thereby compress the leaf springs 82 and 100 and bring the aperture 88 in the plate 68 and the aperture 102 in the plate 92 into alignment as shown in FIG. 6. The leads can now be easily inserted through the plates 68 and 92 and advanced to the point where their metallic terminal portions 34 and 44 are properly engaged by the associated contacts of the connector blocks 38 and 46. By releasing the elongated rubber buttons 74 and 96, the springs 82 and 100 again urge their respective plates 68 and 92 to the point where the edges of their respective apertures squeeze against the deformable plastic insulation coating on the lead body. Because of this engagement between the edges of the apertures and the lead body, a substantial force in excess of three lbs. is found to be required to extract the leads. However, when the buttons 74 and 96 are depressed to bring the apertures in each of the plates into alignment, only a very modest force is required to extract the leads.

It can seen, then, that the above-described lead gripping mechanism is simple in operation and requires no tools for insertion, removal and retention of the lead within the pulse generator's header. The counterbalancing compressive forces of the movable plates 68 and 92 serve to maintain the lead's longitudinal axis aligned with the lead cavity axis. The two countermoving plates containing the eccentric holes, under spring force, apply compressive forces on the lead connector body, thus restraining the lead from involuntary pull-out from the header.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An improvement in an implantable tissue stimulator comprising a pulse generator disposed within a sealed container, a connector header affixed to said container, said header including opposite side surfaces with a longitudinal bore disposed therebetween and with electrical contacts disposed in said bore, and an electrical stimulating lead having an elongated flexible plastic sheath surrounding at least one conductor, said conductor terminating in a proximal pin and ring terminal received in said bore and mating with said electrical contact, the improvement comprising:
   (a) spring biased slide means operably disposed distally from the electrical contacts and traverse to said longitudinal bore and cooperating with said flexible sheath for retaining said pin and ring terminal in said bore.

2. The tissue stimulator as in claim 1 wherein said spring biased slide means comprises:
   (a) first and second parallel slots extending inward from said opposite side surfaces of said connector header transversely to said bore;

(b) first and second plates, each having an aperture individually defined by a perimeter edge and sufficiently large to permit said sheath and said proximal pin and ring terminal to fit therethrough, said first and second plates being disposed in said first and second slots, respectively; and (c) resilient biasing means disposed in said first and second slots and cooperating with said first and second plates for maintaining the aperture in the first plate out of alignment with the aperture in the second plate.

3. The tissue stimulator as in claim 2 and further including means which when squeezed, displaces said first and second plates against said resilient biasing means for bringing said aperture in said first plate into alignment with said aperture in said second plate.

4. The tissue stimulator as in claim 3 wherein said pin and ring terminal can only be inserted into and removed from said bore when said apertures in said first and second plates are squeezed into alignment.

5. The tissue stimulator as in claim 3 wherein the edges defining the apertures in said plates engage and compress said plastic sheath preventing longitudinal movement of said pin and ring terminal within said bore when a portion of said sheath extends through said apertures in said first and second plates and said apertures are non-aligned.

* * * * *